United States Patent [19]
Lombari et al.

[11] Patent Number: 5,245,012
[45] Date of Patent: Sep. 14, 1993

[54] METHOD TO ACHIEVE SOLUBILIZATION OF SPIDER SILK PROTEINS

[75] Inventors: Stephen J. Lombari, Brighton; David L. Kaplan, Stow, both of Mass.

[73] Assignee: The United States of America as represented by the Secretary of the Army, Washington, D.C.

[21] Appl. No.: 953,323

[22] Filed: Sep. 29, 1992

Related U.S. Application Data

[63] Continuation of Ser. No. 511,114, Apr. 19, 1990, abandoned.

[51] Int. Cl.$^5$ .................. C07K 15/20; C07K 3/00; C07K 15/00; C07K 15/08
[52] U.S. Cl. .................................. 530/353; 530/412; 530/422; 530/425; 8/127.6; 8/128.1
[58] Field of Search ............... 530/353, 412, 422, 425; 8/127.6, 128.1

[56] References Cited

U.S. PATENT DOCUMENTS

Re. 21,454  2/1939  Bly et al. ........................... 530/353
4,394,443  7/1983  Weissman et al. .................... 435/6

FOREIGN PATENT DOCUMENTS 294979  12/1988  European Pat. Off.
8803533  5/1988  PCT Int'l Appl.
2162190  1/1986  United Kingdom

OTHER PUBLICATIONS

Work, R. W. and C. T. Young, 1987, The Amino Acid Compositions of Major and Minor Ampullate Silks of Certain Orb-Web-Building Spiders (Araneae, Araneidae), J. Arachnol., 15:65-80.

Abstract entitled: "The Nephila Clavipes Major Ampullate Gland Characterization of Large Polypeptides, Detection of Silk Gene-Related DNA in Nephila Clavipes Genome", S. J. Lombardi & D. L. Kaplan, XI International Congress of Arachnology, Turku, Finland, Aug. 7-12, 1989.

Abstract, accession No. 8118626 of DIALOG File 5; Lombardi et al., 1990, J. Arachnol., 18(3):297-306.

Abstract, accession No. 008445422 of DIALOG File 351 of JP 2240165, published Sep. 25, 1990.

Abstract, accession No. 008287285 of DIALOG File 351 of JP 2113066, published Apr. 25, 1990.

Work et al., 1982, J. Arachnol., 10:1-10.

Dong et al., 1991, Arch. Biochem. Biophys., 284(1);53-57.

Hall, N., 1988, New Scientist, 29:39.

Abstract, Biosir No. 72031529 of Candelas et al., 1981, J. Exp. Zool., 216(1):1-6.

Chemical Abstract No. 67:55000p, of Vecchio et al., 1967.

Chemical Abstract No. 98:199685d of Bhat et al., 1983.

Chemical Abstract No. 89:1875p of Sagar et al., 1978.

Yuen et al., 1989, Biotechniques, 7(1):74-81.

Xu et al., 1990, Proc. Natl. Acad. Sci., 87:7120-7124.

Andersen, "Amino Acid Composition of Spider Silk", Comp. Biochem. Physiol., 35:705-711 (1970).

Gosline et al., "Spider Silk as a Rubber", Nature, 309:551-552 (1984).

Hunt, S., "Amino Acid Composition of Silk from the Pseudoscorpion Neobisium maritimum (Leach): a Possible Link between Silk Fibroins and Keratins", Comp. Biochem. Physiol., 34:773-776 (1970).

Lewis, R. V., "Cloning and Structure of Different Types of Spider Silk", DTIC, AD-A203 137.

Lucas et al., "Comparative Studies of Fibroins. The Amino Acid Composition of Various Fibroins and Its Significance in Relation to their Crystal Structure", Mol. Biol., 2:339-49 (1960).

O'Sullivan, D., "Spider Silk Gene Route to High-tensile Fiber", Chemical and Engineering News, Jul. 25, 1988.

Tillinghast & Christensen, "Observations on the Chemical Composition of the Web of Nephila clavipes, (Araneae, Araneidea)", J. Arachnol., 10:69-74 (1984).

Zemlan, "A Study of the Mechanical Behavior of Spider Silks", Technical Report 69-29-CM, AD 684333, U.S. Army Natick Laboratories, Natick, Mass. 01760-5020 (1968).

Primary Examiner—Keith C. Furman
Attorney, Agent, or Firm—Richard J. Donohue

[57] ABSTRACT

A recombinant spider silk protein can be obtained in a commercially useful form by cloning and the expression in a host cell of a polynucleotide encoding an endogenous spider silk protein or variant thereof. The sequencing of a spider silk protein is made possible by a method for solubilizing a spider silk protein.

3 Claims, 1 Drawing Sheet

```
Ile-Ser-His-Val-Pro-Thr-His-Glu-Asp-Glu¹⁰
ATC-AGT-GAT-GTT-CCA-ACT-CTC-CAA-GAT-GAG³⁰

Ser-Ala-Ala-Val-Gly-Ala-Gly-Ala-Gly-Ala²⁰
AGT-GCT-GCA-GTT-GTT-GCA-GGA-GCA-GGT-GCA⁶⁰

Gly-Ala-Ala-Ala-Gly-Ser-Gly-Ala-Gly-Ala³⁰
GGT-GCT-GCA-GCT-GGT-GCT-GGT-GCG-GGT-GCC⁹⁰
```

FIG. 1

```
Ala-Gly-Ala-Gly-Tyr-Gly-Ala-Ala-Ser-Arg¹⁰
GCT-GGT-GCT-GGT-TAT-GGC-GCT-GCT-AGC-AGG³⁰

CTA-ACA-TGT-GGT-ACC-CCG-GGA-TCC-GGG-CAG⁶⁰

Gly-Phe-Asp-Tyr-Arg-Ile-Arg-Arg-Glu-Gly³⁰
GGC-AAC-GAT-TAT-AGG-ATA-AGA-AGA-GAG-GGA⁹⁰

Tyr-Gly-Gly-Leu-Gly-Arg-Arg-Glu-Gly-Tyr⁴⁰
TAT-GGC-GGT-CTA-GGA-AGA-AGA-GAG-GGA-TAT¹²⁰

Gly-Gly-Leu⁴³
GGC-GGC-TCT¹²⁹
```

FIG. 2

```
Arg-Arg-Glu-Gly-Tyr-Gly-Gly-Leu-Gly⁹
GCA-AGT-GCA-GGT-TCT-GGA-GCT-GGT-TAT²⁷

Ala-Gly-Ala-Gly-Ala-Gly-Ala-Gly-Ala-Gly²⁰
GCT-GGT-GCG-GTT-GCC-GGA-GCT-GGA-GCT-GGT⁶⁰

Tyr-Gly-Ala-Ala-Ser-Gly-Ala-Gly-Ala-Gly³⁰
TAT-GGA-GCT-GCC-TCT-GGT-GCT-GGT-GCT-GGC⁹⁰

Ala-Gly-Glu-Gly-Ala-Gly-Glu-Gly-Gly-Ala⁴⁰
GCT-GGC-GAA-GGC-GCT-GGC-GAG-GGC-GGT-GCT¹²⁰

Gly-Glu-Gly-Glu-Gly-Ala-Gly-Glu-Gly-Ala⁵⁰
GGT-GAA-GGC-GAA-GGC-GCT-GGC-GAG-GGC-GCT¹⁵⁰

Gly-Tyr-Gly-Tyr⁵⁴
GGT-TAT-GGT-TAT¹⁶²
```

FIG. 4

METHOD TO ACHIEVE SOLUBILIZATION OF SPIDER SILK PROTEINS

STATEMENT OF GOVERMENTAL INTEREST

The invention described herein may be manufactured, used and licensed by or for the Government for Governmental purposes without the payment to us of any royalty thereon.

This application is a division of application Ser. No. 511,114 filed Apr. 19, 1990, now abandoned.

BACKGROUND OF THE INVENTION

The present invention relates to producing a spider silk protein, protein fragment or variant, in commercially useful amounts, by means of a recombinant host organism.

There is considerable interest currently in making high-strength, light and versatile fibers. Most high-strength fibers used today, such as Nylon TM and the synthetic ballistic fiber Kevlar TM, have a high density, are expensive and are limited in their range of use. If it were available in commercially useful amounts, a naturally occurring protein could provide an alternative fiber with enhanced properties.

Spider silks have been demonstrated to have several desirable characteristics. For example, spider silk could be used as a light-weight, high-strength fiber for various textile and ballistics applications, as well as for composite materials. Spider silks represent a very diverse group of fibers, particularly with respect to their mechanoelastic properties, which in turn are largely a function of fiber composition and molecular conformation. The spider silks range from those displaying a tensile strength greater than steel (7.8 vs 3.4 G/denier) and those with an elasticity greater than wool (46% vs 43% extension to break) to others characterized by energy-to-break limits that are greater than Kevlar TM ($1 \times 10^5$ vs $3 \times 10^4$ JKG-1).

Considerable difficulty has been encountered in attempting to solubilize and purify natural spider silk while retaining the molecular-weight integrity of the fiber. Another disadvantage of spider silk protein is that only small amounts are available from cultivated spiders, making commercially useful quantities of silk protein unattainable at a reasonable cost.

The term "fibroin" is often used for the silk fibers secreted by some insects and arachnids. See, e.g., Lucas et al., *Adv. Protein Chem.* 13:107-242 (1958). Studies of the chemistry of these fibroins have been reported, for example, by Work and Young, *J. Arachnol.* 15:65-80 (1987). Nevertheless, only limited data are available on the composition of silk fiber from spiders, including those of the genus Nephila. For example, partial amino-acid constituency has been reported for silks of *N. senegalensis* and *N. madagascar lensis*, Lucas et al., *J. Mol. Biol.* 2:339-49 (1960); and *N. clavipes*, Tillinghast & Christensen, *J. Arachnol.* 10: 69-74 (1984). While these investigations suggest that the different Nephila silks vary in composition and properties, there is insufficient information to make a definitive correlation between chemical composition and structural properties.

The silk fibers of Nephila spiders are synthesized by specialized glands situated in the abdominal cavity. Andersen has reported on the amino acid compositions for the seven silks obtained from one animal. See Andersen, *Como. Biochem. Physiol.* 35:705-711 (1970). Of the seven types of silks, only two have been investigated in any detail, and no sequence data were obtained.

In addition to the problem of solubility, multiple forms of spider silks are produced simultaneously by any given spider. The resulting mixture is much less useful than a single isolated silk because the different spider-silk proteins have different properties and, due to solubilization problems, are not easily separated by methods based on their physical characteristics.

Accordingly, at least three major problems have inhibited consideration of the feasibility of producing spider silk fibers with desirable characteristics, in commercially useful quantities, for use as components of textile, composite and ballistic materials. First, an effective means for solubilizing silk protein has been unavailable heretofore, making amino-acid sequencing of the protein virtually impossible. As a corollary, it has not been possible to identify, isolate and clone a spider silk-encoding DNA into a suitable expression system. Nor has it been feasible to produce a spider silk protein in quantities much greater than can be obtained naturally from spiders. Consequently, there has been a need but no means for providing commercially useful quantities of spider silk protein in a form displaying homogeneous mechanoelastic properties.

SUMMARY OF THE INVENTION

It is therefore an object of the present invention to provide commercially useful quantities of a homogeneous spider silk protein. In this regard, a "homogeneous" silk-protein composition is one that, while possibly containing more than one type of fiber, possesses uniform mechanostructural properties such as tensile strength, energy required to break a fiber, elasticity, ballistic limit and modulus.

Another object of the present invention is to provide a method for producing a recombinant spider silk protein in recoverable amounts.

Yet another object of the present invention is to provide a method for solubilizing a spider silk protein.

In accomplishing the foregoing objectives, there has been provided, in accordance with one aspect of the present invention, an isolated spider silk protein comprising an amorphous domain or subunit and a crystalline domain or subunit. In this context, a domain refers to a portion of an endogenous protein that provides particular mechanostructural properties to the protein and a subunit refers to a given amino-acid sequence that is repeated in the protein.

In a preferred embodiment, a crystalline domain or subunit comprises the amino-acid sequence Ala-Gly-Ala-Gly-Ala-Gly-Ala-Gly-Tyr-Gly-Ala-Gly-Ala -Gly-Ala-Gly-Ala-Gly-Ala-Gly-Tyr-Gly-Ala-Ala-Ser -Gly-Ala-Gly-Ala-Gly-Ala-Gly-Glu-Gly-Ala-Gly-Glu -Gly-Gly-Ala-Gly-Glu-Gly-Glu-Gly-Ala-Gly-Glu-Gly -Ala-Gly-Tyr-Gly-Tyr. In another preferred embodiment, an amorphous domain or subunit comprises the amino-acid sequence Ala-Gly-Ala-Gly-Tyr-Gly-Ala -Ala-Ser-Arg-Leu-Thr-Cys-Gly-Thr-Pro-Gly-Ser-Gly -Gln-Gly-Phe-Asp-Tyr-Arg-Ile-Arg-Arg-Glu-Gly-Tyr -Gly-Gly-Leu-Gly-Arg-Arg-Glu-Gly-Tyr-Gly-Gly-Leu. In alternative preferred embodiment an amorphous domain or subunit comprises the amino-acid sequence Arg-Arg-Glu-Gly-Tyr-Gly-Gly-Leu-Gly. In a further preferred embodiment, a spider silk protein or variant has an N-terminal sequence of Ile-Ser-His-Val-Pro-Thr-His-Glu-Asp-Glu-Ser-Ala-Ala -Val-Gly-Ala- Gly-Ala-Gly-Ala-Gly-Ala-Ala-Ala-Gly -Ser-Gly-Ala-Gly-Ala.

In accordance with another aspect of the present invention a homogeneous spider silk protein composition is provided. Such a composition can comprise an isolated spider silk protein or spider silk variant having at least one crystalline domain and at least one amorphous domain. Another aspect of the present invention to provide an isolated spider silk protein or variant wherein the ratio of the crystalline domain to the amorphous domain is greater than 1, such that the tensile stength of the resulting spider silk is increased. Alternatively, the ratio of the crystalline domain to the amorphous domain is less than 1, such that the elasticity of the resulting spider silk is increased. Another aspect of the present invention is to provide an isolated spider silk protein or variant that is in substantially pure form.

Still another aspect of the present invention is to provide a polynucleotide encoding a spider silk protein or variant, a vector comprising such a polynucleotide, such that the vector can be selected form the group consisting of a viral vector, a phage vector, a cosmid, and a plant vector. In addition the present invention provides a host cell comprising a polynucleotide as described above, selected from the group consisting of a bacterial cell, an insect cell, a yeast cell, a mammalian cell, and a plant cell.

An additional aspect of the present invention is to provide a method for producing a recombinant spider silk protein comprising the steps of providing a host cell comprising an isolated polynucleotide encoding a spider silk protein or variant, culturing the host cell such that said spider silk protein or variant is expressed by said host cell in recoverable amounts; and recovering the spider silk protein or variant.

Another aspect of the present invention is to provide a method for solubilizing a spider silk protein or variant, comprising the steps of providing a sample comprising at least one spider silk protein or variant, contacting the said sample with a solution consisting essentially of propionate and hydrochloric acid in a 50%—50% volume per volume (v/v) ratio, and solubilizing the spider silk protein or variant in the solution to obtain a solubilized spider silk protein, such that the solubilized spider silk protein is susceptible to amino-acid sequencing.

Other objects, features and advantages of the present invention will become apparent to those skilled in the art from the following detailed description. It should be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications. Unless otherwise indicated, the respective contents of the documents cited below are hereby incorporated by reference.

BRIEF DESCRIPTION OF THE DRAWINGS

The present invention may be more readily understood by referring to the accompanying drawings by which FIG. 1 depicts an amino-acid sequence and corresponding anti-sense cDNA sequence of the N-terminus of a exemplary spider silk protein.

FIG. 2 depicts a an exemplary spider silk protein or variant amorphous domain or subunit and corresponding anti-sense cDNA sequence.

FIG. 3 depicts an alternative dragline silk protein amorphous domain or subunit and corresponding anti-sense cDNA sequence.

FIG. 4 depicts a portion of a dragline silk protein or variant crystalline domain or subunit and corresponding anti-sense cDNA sequence.

In these drawings, an anti-sense cDNA sequence corresponds to the encoding mRNA sequence except that "T" in a cDNA sequence designates a thymine base, while, in the corresponding RNA sequence, T is replaced with "U" to designate a uracil base.

DETAILED DESCRIPTION OF THE PREFERRED EMBODIMENTS

Pursuant to the present invention, spider silk proteins can be solubilized in a manner that permits their sequencing and purification. Moreover, the sequence information thereby obtained enables the cloning of spider silk-encoding DNA and the heterologous expression of spider silk proteins in commercially useful quantities. Polypeptides of the present invention therefore include recombinant spider silk proteins, as well as fragments and variants thereof, as defined below, that are commercially useful as components of textile, composite and ballistic materials. By the same token, the present invention includes polynucleotides that code for such spider silk proteins and variants.

More specifically, a method within the present invention for producing a recombinant spider silk protein or variant involves the steps of providing a host cell having a heterologous polynucleotide which encodes a spider silk protein, culturing the host cell under conditions such that the protein can be produced by the host cell in recoverable amounts, and recovering the protein in a substantially pure form that is suitable for commercial applications.

A "recoverable" amount in this regard means that an isolated amount of a spider silk protein can be detected by a methodology less sensitive than radiolabeling, such as an immunoassay, and can be subjected to further manipulations involving transfer of the protein per se into solution. Preferably, a recoverable amount of a spider silk protein or variant should be an amount such that transferring the protein into solution yields a concentration of at least 50 nM, preferably at least 50 µM.

According to the present invention, spider silk proteins can be solubilized without disrupting protein structure to the extent that the molecular-weight integrity of the protein is compromised. Solubilization to this end involves the use of concentrated hydrochloric acid (HCl) of at least 6N concentration, optionally in conjunction propionic acid. In one embodiment, soluene can be used as a less efficient solvent, but which is capable of partially dissolving a spider silk protein or variant. In a preferred embodiment, the spider silk protein is contacted with constantly boiling mixture of 6N HCl and 50% propionic acid (50:50, v/v). An acid mixture of this constituency dissolves spider silk protein and provides a clear, nonviscous solution which is suitable for use in determining amino acid sequence by known methods, such as Edman degradation or hydrolysis-HPLC.

Spider silk proteins and variants of the present invention have commercially useful properties, suitable for textile, composite and ballistic materials, including desirable tensile strength, elasticity, ballistic limit, and modulus. The properties of a spider silk protein or variant of the present invention is determined by the relative ratio of the amorphous and crystalline domains or subunits. Modification of the relative and total amounts of these amorphous and crystalline domains or subunits in a recombinant spider silk protein of the present invention provide improved commercially useful properties, as described above. Examples of how modifications in this relative ratio will affect these properties include increased tensile strength by increasing the crystalline to amorphous domain ratio, increased elasticity by either increasing the amorphous to crystalline ratio or decreasing the occurrence of Ala-Ala dipeptides in the crystalline domains. These modifications of the structure of an endogenous spider silk protein can be accomplished by conventional procedures such as site-directed or cassette mutagenesis of isolated polynucleotides that encode functional portions of a spider silk protein or variant.

A recombinant spider silk protein of the present invention can be obtained in recoverable amounts in a form such that the spider silk protein preparation migrates as a single band on a silver stained and commassie blue stained SDS-PAGE gel ("substantially pure form"). In terms of relative purity, a preferred form of a recombinant spider silk protein is one that provides a single peak in a conventional high-performance liquid chromatography column.

Based on the nucleotide sequences that encode polypeptides, e.g., as set out in FIGS. 1-4, and on knowledge regarding newly characterized amorphous and crystalline domains of spider silk proteins, polypeptide molecules can also be produced which represent variations of the naturally occurring molecule. The characterization of these crystalline and amorphous domains or subunits is carried out by analysis of the discovered amino acid sequences of a spider silk protein. The crystalline domains or subunits of a spider silk protein or variant of the present invention are characterized by comparison of the discovered spider silk protein amino acid sequence with known crystalline domains of *Bombyx mori*. See, e.g., Iizuka *Biorheology* 3:551-552 (1965). Alternatively, the amorphous domains or subunits are characterized by finding repeated, non-crystalline sequences within the discovered spider silk amino acid sequences.

These polypeptide molecules that contain variations of the ratio and amounts of endogenously occuring amorphous and crystalline domains are referred to here generically as "spider silk variants" and include, for example, spider silk muteins and molecules that correspond to portions of a spider silk protein. The key to diversifying the silks is in altering the genetic makeup of the silk-encoding polynucleotide to tailor the physicochemical makeup of the expressed spider silk polypeptide for various fiber applications.

In this regard, a "spider silk mutein" is a polypeptide that retains the basic structural attribute of spider silks—namely, at least one repeated amino-acid sequence representing an amorphous and/or a crystalline subunit of an endogenous silk protein—and a commercially useful mechanoelastic property of a spider silk protein. A spider silk mutein can also be homologous to an endogenous spider silk protein. "Homology" in this context connotes a degree of similarity in amino acid sequence, relative to an endogenous spider silk, such that the mutein in question displays typifying mechanostructural properties that are like those of the endogenous protein.

Spider silk muteins can be produced, in accordance with the present invention, by conventional site-directed or cassette mutagenesis, two avenues for routinely identifying residues of a spider silk protein which can be modified without adversely affecting particular mechanoelastic properties. See Ausubel et al., CURRENT PROTOCOLS IN MOLECULAR BIOLOGY (John Wiley & Sons 1987, 1990) (hereafter "Ausubel") at §8. Oligonucleotide-directed mutagenesis, comprising [i] synthesis of an oligonucleotide with a sequence that contains the desired nucleotide substitution (mutation), [ii] hybridizing the oligonucleotide to a template comprising a structural sequence coding for a spider silk protein or variant and [iii] using T4 DNA polymerase to extend the oligonucleotide as a primer, is preferred because it is readily applied in determining the effect(s) of particular changes to a spider silk protein structural sequence. Its relative expense may militate in favor of an alternative, known direct-mutagenesis method.

A spider silk variant that correspond to a portion of a spider silk protein would be a polypeptide containing the amino-acid sequence that corresponds to at least one repeating structural unit of an amorphous or crystalline domain of a spider silk protein, absent the other structural portions. In this context, the ratio of amorphous and crystalline domains or subunits could be increased or decreased to provide a recombinant spider silk variant that had varied mechanostuctural properties, as desired for a particular textile, composite or ballistic material. For example, decreasing the ratio of amorphous subunits to crystalline subunits can increase the tensile strength of a spider silk variant according to the present invention.

Examples of crystalline and amorphous domains are those of a spider dragline silk from *Nephila clavipes*, wherein a crystalline domain or subunit can comprise the amino-acid sequence Ala-Gly-Ala-Gly -Ala-Gly-Ala-Gly-Tyr-Gly-Ala-Gly-Ala-Gly-Ala-Gly -Ala-Gly-Ala-Gly-Tyr-Gly-Ala-Ala-Ser-Gly-Ala-Ala -Gly-Glu-Gly-Glu-Gly-Ala-Gly-Glu-Gly-Ala-Gly-Tyr-Gly-Tyr. An amorphous domain or subunit can similarly comprise the amino-acid sequence Ala-Gly-Ala -Gly-Tyr-Gly-Ala-Ala-Ser-Arg-Ile-Thr-Cys-Gly-Thr -Pro-Gly-Ser-Gly-Gln-Gly-Phe-Asp-Tyr-Arg-Ile-Arg -Arg-Glu-Gly-Tyr-Gly-Gly-Leu-Gly-Arg-Arg-Glu-Gly-Tyr-Gly-Gly-Leu. An alternative amorphous domain or subunit can also comprise the amino-acid sequence Arg-Arg-Glu-Gly-Tyr-Gly-Gly-Leu-Gly. A recombinant spider silk protein or variant can have an N-terminal sequence of Ile-Ser-His-Val-Pro-Thr-His -Glu-Asp-Glu-Ser-Ala-Ala-Val-Gly-Ala-Gly-Ala-Gly -Ala-Gly-Ala-Ala-Ala-Gly-Ser-Gly-Ala-Gly-Ala.

Other spider silk variants within the present invention can be fragments of the cloned and expressed molecule that retain at least one commercially useful mechanoelastic property of a spider silk protein, and that are homologous to a spider silk protein. Such fragments could be produced by known de novo-synthesis techniques and by fragmentation of the spider silk protein molecule itself, as well as by producing a genetically-engineered vector/host cell system that expresses a spider silk protein fragment encoded by a heterologous polynucleotide used to transform the host.

To be used in recombinant expression of a spider silk protein or a spider silk protein variant, a polynucleotide molecule encoding a spider silk protein or a spider silk protein variant would preferably comprise a nucleotide sequence, corresponding to a desired amino-acid sequence, that is optimized for the host cell of choice (see below) in terms of codon usage, initiation of translation and expression of recoverable amounts of a commercially useful spider silk protein or a spider silk protein variant. Also, the vector selected for transforming a chosen host organism with such a polynucleotide molecule should allow for efficient maintenance and transcription of the sequence encoding the polypeptide.

Vectors can be used for cloning and expression of a polynucleotide according to the present invention in a host cell. Such vectors can be derived, for example, from a bacteria, a virus, a filamentous phage (such as a M-13 derived phage), a cosmid, a yeast or a plant. Vectors will preferably include a replicator, a selectable marker, and a cloning site. See Ausubel at § 1.51. Protocols for obtaining and using such vectors are known to those in the art. Ausubel at §§ 1.5-1.15, 9.1-9.6 and 13.4-13.11.

Examples of bacteria-derived vectors include plasmid vectors such as pBR322, pUC19, pSP64, pUR278 and pORF1. Ausubel at § 1.5. Illustrative of suitable viral vectors are those derived from phage, vaccinia, retrovirus, baculovirus, or a bovine papilloma virus. Examples of phage vectors include λ+, λEMBL3, λ2001, λgt10, λgt11, Charon 4a, Charon 40, and λZAP/R. See id. at §§ 1.10-1.12. pKB3 and pSC11 are exemplary of vaccinia vectors (see, e.g., Chakrabarti et al., *Molec. Cell. Biol.* 5:3401-9 (1985) and Mackett et al *J. Virol.* 49:857-864 (1984). Suitable retroviral vectors can also be used. See Hollis et al., *Nature* 296:321-325 (1982). Among illustrative baculovirus vectors are pAcRP23, described in Matsuura, *J. Gen. Virol.* 68:1233-50 (1987) and in Possee & Howard, *Nucl. Acid Res.* 15:10233-48 (1987). An example of a filamentous phage vector is an M13-derived vector like M13mp18, M13mp19/pUC19, M13mp18/pUC18, M13mp10/pUC13, M13mp10/pUC12 and M13mp7/pUC7. See Ausubel at §1.14. Examples of a yeast vector include Ylp5, YRp7, YEp24, 2 μm plasmid, YCp50, pYAC3 and Trichoderma reesei. Ausubel, §§13.4-13.6. Alternatively, bovine papilloma-derived vectors can be used. See, e.g., Dimaio et al *Proc. Nat'l Acad. Sci. USA* 79:4030-4034 (1982) and Sekiguchi et al *Gene* 21:267-272 (1983).

When most or all of a relatively long polynucleotide (for example, > 10kb) encoding a spider silk protein is expressed according to the present invention, vectors are preferably selected that express such long polynucleotides efficiently. For example, in the case of a polynucleotide encoding a dragline silk protein of *N. clavipes*, the golden orb-weaving spider (see below), the polynucleotide is about 12 kb long. Suitable vectors for expressing such a polynucleotide include those that efficiently express a polynucleotide that is greater than 11 kb, e.g., phage vectors such as EMBL3 or gt11 or yeast vectors such as 2 μm plasmid or pYACC3. See Ausubel at §§1.10 and 13.4.

According to the present invention, DNA that encodes a spider silk protein or variant can be isolated and expressed in a recombinant microbe or other organism, by known procedures, to produce the desired polypeptide in commercially useful amounts. Such a DNA can be isolated by screening nucleic acid libraries generated from microorganisms expressing a spider silk protein or variant according to the present invention. See Ausubel at §§5 and 6. These libraries can be screened using oligonucleotide probes that are complementary to a polynucleotide encoding, e.g., a portion of the N-terminus or known domains of a spider silk protein or variant of the present invention, e.g., as a crystalline domain comprising a portion of the amino acid sequence depicted in FIG. 4, such as GGC-GAA-GGC-GCT-GGC-GAG-GGC-GGT-GCT; an amorphous domain comprising a portion of an amino acid sequence depicted in FIG. 1, such as GGA-TAT-GGC-GGT-CTA-GGA or an alternative amorphous domain comprising an amino-acid sequence Arg-Arg-Glu-Gly-Tyr-Gly-Gly-Leu-Gly. In a further preferred embodiment, the spider silk protein has an N-terminal sequence of Ile-Ser-His-Val-Pro-Thr-His-Glu -Asp-Glu-Ser-Ala-Ala-Val-Gly-Ala-Gly-Ala-Gly-Ala-Gly-Ala-Ala-Ala-Gly-Ser-Gly-Ala-Gly-Ala. See Ausubel at §6.

Alternatively, other portions including or adjacent to an endogenous coding sequence of a spider silk protein or variant according to the present invention can be used, when isolated using a probe as a template for generating other probes useful for isolating a spider silk protein or variant-encoding polynucleotide according to the present invention, e.g., based on the N-terminal, crystalline or amorphous domain sequences described above. Such a probe can be used by known procedures for screening a genomic or cDNA library as described above, or as a basis for synthesizing PCR probes for amplifying a cDNA generated from an isolated RNA encoding a spider silk protein or variant according to the present invention. For example, transformants can be selected for expression by a host cell of a spider silk protein or variant, by use of selection media appropriate to the vector used, RNA analysis or by the use of antibodies specific for a spider silk protein according to the present invention. See, e.g., Ausubel at §§9.5.2 (selectable markers), §9.8 (RNA analysis), §§10.6-8 (detection of proteins), §§11.1-1.2 (immunoassays) and §§11.3-.16 (preparation and use of monoclonal, polyclonal and antipeptide antibodies for protein detection).

Such a cDNA can then be cloned into a suitable expression vector and used to transform a host cell, as described below. See Ausubel at §15.4. Suitable host cells in this context include prokaryotic cells (bacterial or blue-green algal) and eukaryotic cells such as yeast, insect, mammalian and human cells. Suitable host cells of the present invention can preferably include microorganisms, e.g., of the genera Aeromonas, Aspergillus, Bacillis, Escherichia, Kluyveromyces, Pichia, Rhodococcus, Saccharomyces and Streptomyces. Illustrative of microorganisms used as host cells according to the present invention include, as bacterial cells, *E. coli* and Bacillus, and as yeast cells, *Saccharomyces cerevisiae* strains X2181-1B, with genotype α trp1 gal1 ade1 his2 (available from the Yeast Genetic Stock Center, Berkeley, Calif.); strain ATCC 52683, with genotype α his2 ade1 trp1 met14 ura 3 (aka strain "J17," available from the American Type Culture Collection, Rockville, Md.); and strain ATCC 46183, with genotype α his1 trp1 (aka "strain IL166-5B," also available from the American Type Culture Collection).

For introducing a polynucleotide of the present invention into a bacterial cell, known procedures can be used according to the present invention such as by transfection, e.g., using calcium phosphate precipitation, electroporation, DEAE dextran, pelletizing with a DNA gun or using a recombinant phage virus. See Ausubel, at §1.8. Other known procedures can also be employed to obtain a recombinant host cell that expresses a heterologous spider silk protein according to the present invention, as will be apparent to those skilled in the art.

For introducing a polynucleotide of the present invention into a yeast cell, the most commonly used protocol, the lithium acetate method, exploits the fact that alkali cations make yeast cell membrane permeable to DNA; in addition, uptake of foreign DNA is promoted by the presence in the medium of a high-molecular-weight molecule, polyethylene glycol. An alternative method, spheroplast transformation, can be used but is more time-consuming than the lithium acetate procedure, though it results in a higher efficiency of transformation per input DNA.

Another type of suitable expression system of the present invention entails the use of a mammalian host cell transformed with a polynucleotide within the present invention. Suitable vectors can be used that express a spider silk protein or variant efficiently in mammalian host cells such that the protein is expressed in commercially useful quantities. Illustrative of suitable mammalian-cellular hosts which can be used for this purpose are Chinese ovary (CHO) cells as described by Urlaub & Chasin, *Proc. Nat'l Acad. Sci. USA* 77:4216 (1980) and baby hamster kidney (BHK) cells, exemplified by a cell line deposited under accession number ATCC CCL 10 and another line ATCC CCL 70.

For both yeast and mammalian expression systems, there are conventional transformation and screening protocols which can be employed pursuant to the present invention. Standard methodology in this regard is detailed in Ausubel, supra, at §§9 and 13.

For baculoviral expression systems, conventional transformation procedures with pACRP-derived vectors are used to transform suitable host cells including those of, e.g., Spodoptera (such as sf9 cells), Trichoplusia, and heliothis. See Luckow & Summers, *Biotechnology* 6:47–55 (1988); Miller, *Ann. Rev. Microbiol.* 42:177–199 (1988); Maeda, *Ann. Rev. of Microbiol.* 34:351–72 (1989). For vaccinia viral expression systems, see Chakrabarti et al., *Molec. Cell. Biol.* 5:3401–9 (1985) and Mackett et al., *J. Virol.* 49:857–864 (1984). While the foregoing represents preferred methods and materials for expressing spider silk proteins according to the present invention, it will be apparent to those of skill in the art that many alternative methods are suitable for expressing such a protein according to the present invention.

Introduction of a polynucleotide of the present invention into mammalian cells to produce a recombinant cell which expresses a spider silk protein or variant can be accomplished according to conventional procedures, such as by calcium phosphate or DEAE-dextran transfection. See, e.g., Ausubel, supra, at §9. Expression of such recombinant cells of the present invention provides recoverable amounts of a spider silk protein or variant.

Host cells comprising a polynucleotide which encodes a spider silk protein or variant of the present invention can be grown under conditions that provide expression of a desired polypeptide in recoverable or commercially useful amounts. See id., §§ 1 and 13.

An example of a silk spider protein suitable for solublization according to the present invention is the silk of the golden orb-weaving spider, *N. clavipes*, a large spider found in the tropical and subtropical areas of the western hemisphere. Moore, *Am. Mid. Natur.* 98:95–108 (1977). This species produces five to seven different silk proteins, but it is the major ampullate gland silk (dragline) that possesses the highest strength. Three morphological regions distinguish the major ampullate gland: the tail, the sac and the duct. The tail is the site of about 90% of the major ampullate gland's protein synthesis activity; the ampulla is a storage site for soluble dragline silk; and the duct appears to be involved with secretion and ordering of silk. Bell & Peakall, *J. Cell Biol.* 42:285–95 (1969).

Major ampullate glands of *N. clavipes*, as in other spiders, can be dissected and messenger RNA (mRNA) from the gland isolated and purified, in accordance with the present invention, by oligo d(T) cellulose chromatography. Dragline silk cDNA can then be constructed by reverse-transcribing the gland mRNA.

In order to clone and express commercially useful amounts of a spider silk protein, such as Nephila dragline silk, a portion of the amino-acid sequence of the natural protein can be determined, e.g., by Edman degradation, and synthetic oligonucleotide probes can be constructed based on this sequence information, taking into account the redundancy of the codons encoding such a protein. mRNA can be isolated by known procedures (See, e.g., Id., at §4) from the major ampullate gland which produce a silk protein. The mRNA is then reversed transcribed to construct a cDNA library, followed by screening with the above-mentioned probes (see, e.g., Ausubel, at §§5 and 6, respectively).

The synthesized cDNA can be cloned into an expression vector and the lambda gt11 Sfi-Not vector (available from Promega Biotech) can be employed. Lambda gt11 Sfi-Not DNA is thus used as a vector for orientation-specific cDNA cloning, allowing the expression of cloned inserts as polypeptides fused with β-galactosidase. Directional cloning can be achieved by using a unique oligodeoxynucleotide primer-adapter containing the recognition site for NotI upstream from an oligo(dT) sequence to prime first strand synthesis. After second strand synthesis and ligation of either EcoRI linkers or adapters, the double stranded molecules can be digested with NotI (and EcoRI for linkers). Following removal of excess linker/adaptor fragments, the spider silk cDNA is ready to ligate into the provided EcoRI-NotI vector arms.

Recombinant phage can then be recognized by their ability to form colorless plaques when plated on lachosts (*E. coli* Y1089(r-) and Y1090(r-)) in the presence of X-GAL (5-bromo-4-chloro-3-indolyl-β-galactopyranoside). By this method, the spider silk cDNA molecules can be cloned in the same orientation relative to the lacZ gene, which can effectively double the likelihood of in-frame expression of cloned silk genes as fusion proteins. This strategy can increase the possibility of successful isolation of specific cDNA clones using nucleic acid or antibody probes.

Dragline silk clones can be further isolated by using nucleic acid probes constructed specifically from dragline silk protein sequences. Once identified, these clones can be repurified to ensure purification of only the dragline silk cDNA. Positive clones can be sequenced and the overlapping sequences can be used to determine the full length nucleic acid sequence that encodes a dragline silk protein of Nephila. See Ausubel at §§ 6 and 7. The full length cDNA can then be reconstructed from the cloned fragments. Id. at §3.16.

This cDNA can be expressed in *E. coli* or other suitable host organism, and the presence of the resultant silk/β-GAL fusion protein can be ascertained, for example, by immunoscreening, thereby to identify recombinants which produce the protein. Selected clones can then be cultured and tested, for example, by western blotting for the presence of the protein. The protein can be purified in a conventional manner, either from the host medium or from a preparation of lyzed host cells, for example, by using an immunoaffinity adsorbent column. By this approach, dragline spider silk protein from the species *Nephila clavipes* was found to have a molecular weight of about 350,000 daltons and is encoded by a polynucleotide of about 12,000 daltons.

The present invention is further described by reference to the following, illustrative examples. In these examples, specimens of the following arachnid species were used: *N. clavipes* Nephilinae, supplied by Angela Choate (USDA, Gainesville, Fla.); *Argiope aurantia* Lucas and *Neoscona domiciliorum* Hentz, supplied by Mark Stowe, (University of Florida, Gainesville). Live specimens were housed in individual cages and fed a diet of german cockroaches, *Blatella germanica* (Blattellidae). Some specimens were frozen in liquid nitrogen and stored at −70° C. for subsequent nucleic acid extractions.

EXAMPLE 1

Silk Collection

Samples were collected from the aranaid species *N. clavipes* Nephilinae, *Arglope aurantia* Lucas, and *Neoscona domicilicorum* Hentz. Controlled silking was performed as described by Work and Emerson, supra (1982). Controlled silking was restricted to the spiders which were large enough to be easily manipulated without damaging the spider. The silking procedure consistently averaged 5 to 30 minutes and 5.0–10.0 milligrams (mg) of major ampullate silk gland was routinely obtained. The mature female was continuously observed under 60× magnification to substantiate the glandular source of silk. All reeled samples were examined using a light microscope (100× objective, 12.5× ocular; 1250× total magnification) to ensure that there was no contamination by minor ampullate gland fibers.

EXAMPLE 2

Silk Solubilization

Silk samples (approximately 1.0–2.0mg) were placed in 13×100mm sterile glass borosilicate test tubes. The solvents listed in Table 1 were added to a final concentration of 1.0 ug/ul and solubility determined visually at room temperature.

TABLE 1

| Solubility of *Nephila clavipes* dragline silk in various solvent systems. | |
|---|---|
| Solvent | Solubility at Room Temperature |
| Water | −1 |
| 1N HCl | −1 |
| 2N HCl | −1 |
| 3N HCl | −1 |
| 4N HCl | −2 |
| 5N HCl | −2 |
| 6N HCl | −1/+2 |
| 1N KOH | −1 |
| Chloroform | −1 |
| Ethyl alcohol 95% | −1 |
| 8M Urea | −2 |
| 50% Lithium Bromide | −2 |
| 1% SDS | −1 |
| 5% Mercaptoethanol | −1 |
| Soluene | +3 |
| Boiling 5N HCl/50% Propionic Acid | ++4 |

1. Totally insoluble
2. Partially soluble, some particulates
3. Partially soluble, no particulates, viscous suspension
4. Totally soluble, no particulates, clear, non-viscous Of the solubilizing agents studied, only hydrochloric/propionic acid (50:50, v:v) dissolved *N. clavipes* dragline silk at room temperature with only slight agitation (Table 1). Hydrochloric acid below 6N and used alone failed to completely dissolve the silk even at elevated temperatures (data not shown). Some quaternary ammonium compounds used as commercial tissue solubilizers proved to be efficient solvents, but the solvent could not be easily removed from the solution. High concentrations of base also dissolved silk samples, although they were not used because the elevated temperatures needed for solubilization may begin random hydrolysis of the silk backbone prior to amino acid hydrolysis. Any amino acids hydrolyzed prior to the 150° C. hydrolysis reaction may then become completely degraded at the hydrolysis step and subsequently unaccounted for in the final analysis.

Hydrochloric/propionic acid proved to be most suitable. The silk thus dissolved retained its structural integrity, having the same molecular-weight value as that determined by polyacrylamide gel electrophoresis and high performance liquid chromatography.

EXAMPLE 3

Silk Hydrolysis

Major ampullate gland silk samples (2.0 mg) were first dissolved in 2.0 ml of a hydrochloric/propionic acid mixture at room temperature for 20 min with slight vortexing. Solubilized samples (100 µl at 1.0 µg/µl) were vacuum dried in pyrolyzed vials and purged with argon gas. Hydrolysis was carried out by placing 200 µl of constant boiling 6N HCl in the bottom of an acid-resistant reaction vessel along with 2 sodium sulfite crystals. The vessel was again purged with argon gas, sealed under vacuum and placed at 150° C. for 1 hour. Argon was used as a purging gas because of its purity and because it contributes fewer artifact peaks in the subsequent analysis. Sodium sulfite was discovered to be useful as an oxygen scavenger and aids in the recovery of cysteine, serine, and threonine (Ted Tanhauser, Cornell University, personal communication).

Multiple analyses were carried out on a Waters HPLC Pico-Tag Amino Acid analysis system. The hydrolyzed samples were derivatized with phenylisothiocyanate (PITC) and these samples reconstituted in 400 µl of sample diluent. For each analysis a 50 µl injection volume was used. Amino acid standards were run with each sample. Ribonuclease A was run as an hydrolysis control.

EXAMPLE 4

Amino Acid Analysis

The amino acid composition of the secretion of (MaAS) from *N. clavipes* is shown in Tables 2 and 3. Glycine, alanine, glutamic acid/glutamine and arginine were the most abundant amino acids, comprising 74% of all amino acids present. Generally, the major ampullate gland silk has been considered for use in the production of dragline and frame threads of the web. The dragline has a high tensile strength (198 grams per denier, gpd) and it has a rupture elongation of 18%, determined according to Zemlin, *Technical Report* 69-29-CM, AD 684333 10760-5020 (1967). The composition of the material from the large ampullate gland generally agrees with the published analyses of dragline from *N. clavipes*, see Zemlin, loc. cit., and Work & Young, *J. Arachnol.* 15:65–80 (1987), but some differences were observed.

Table 3 shows the amounts of various amino acid side chains in dragline silk of N. clavipes. Dragline silk is composed predominantly of the small side-chain amino acids glycine, alanine and serine, which would allow them to conform to the antiparallel beta-pleated sheet model proposed by Pauling and Corey, *Proc. Nat. Acad. Sci.* 39:253–256 (1953), for *Bombyx mori*. The conformational model applies only to the crystalline regions of *B. mori*, which makes up approximately 40% of the total silk structure, as determined by x-ray diffraction analysis according to Lizuka, *Biorheology* 3:551–552 (1965). Limited x-ray diffraction data has been reported, however, that indicate the degree of crystallinity in dragline silk of certain araneid species. See Gosline et al., *Nature* 309:551–552 (1984).

TABLE 2

| Amino acid composition of the silk gland secretion of *Nephila clavipes*. Results expressed as residues per 100 total. | | | | |
|---|---|---|---|---|
| Dragline Trials | | spider 1 3 | spider 2 3 | spider 3 3 |
| Asp/Asn | (D/N) | 2.5 | 2.4 | 2.6 |
| Glu/Gln | (E/Q) | 9.1 | 9.0 | 9.2 |
| Ser | (S) | 4.5 | 4.5 | 4.4 |
| Gly | (G) | 37.0 | 37.3 | 36.9 |
| His | (H) | 0.5 | 0.4 | 0.4 |
| Arg | (R) | 7.6 | 7.6 | 7.7 |
| Thr | (T) | 1.6 | 1.7 | 1.6 |
| Ala | (A) | 21.1 | 21.0 | 21.2 |
| Pro | (P) | 4.3 | 4.3 | 4.3 |
| Tyr | (Y) | 3.0 | 3.0 | 3.2 |
| Val | (V) | 1.8 | 1.8 | 1.7 |
| Met | (M) | 0.3 | 0.3 | 0.2 |
| Cys | (C) | 0.1 | 0.1 | <0.1 |
| Ile | (I) | 1.0 | 1.0 | 1.0 |
| Leu | (L) | 3.8 | 3.7 | 3.7 |
| Phe | (F) | 0.7 | 0.7 | 0.6 |
| Lys | (K) | 1.0 | 1.0 | 1.0 |

TABLE 3

| Amounts of various amino acid side chains in silk gland secretions of *Nephila clavipes*. Results expressed as residues per 100 total. | | | |
|---|---|---|---|
| Dragline silk Trials | spider 1 3 | spider 2 3 | spider 3 3 |
| small side chains | 62.28 | 62.92 | 62.59 |
| polar side chains | 29.81 | 29.61 | 30.22 |
| acidic/amide side chains | 11.67 | 11.52 | 11.83 |
| basic side chains | 9.05 | 9.02 | 9.06 |
| cyclic imino side chain | 4.3 | 4.34 | 4.28 |
| aromatic side chain | 3.62 | 3.57 | 3.88 |
| sulfur containing | 0.47 | 0.46 | 0.22 |
| aliphatic side chain | 27.61 | 27.57 | 26.62 |
| hydroxyl side chain | 6.16 | 6.20 | 6.09 | small side chains: gly+ala+ser
polar residues: asp+thr+ser+glx+tyr+lys+his+arg
acidic/amide residues: asx+glx
basic side chains: lys+his+arg
cyclic imino side chain: pro
aromatic side chain: phe+tyr
sulfur containing: met+cys
aliphatic side chain: ala+val+leu+ile
hydroxyl side chain: ser+thr

EXAMPLE 5

Cloning of a Spider Silk Protein

A dragline silk of Nephila, as described in EXAMPLES 1–4 above, was sequenced by Edman degradation, and synthetic oligonucleotide probes were constructed that corresponded to this sequence, as shown in FIG. 1, taking into account the redundancy of the codons encoding such a protein. A crystalline domain of the spider silk protein was thus determined to have an amino-acid sequence of Ala-Gly-Ala-Gly-Ala-Gly-Ala-Gly-Tyr-Gly-Ala-Gly-Ala -Gly-Ala-Gly-Ala-Gly-Ala-Gly-Tyr-Gly-Ala-Ala-Ser -Gly-Ala-Gly-Ala-Gly-Ala-Gly-Glu-Gly-Ala-Gly-Glu    -Gly-Gly-Ala-Gly-Glu-Gly-Glu-Gly-Ala-Gly-Glu-Gly-Ala-Gly-Tyr-Gly-Tyr. The probes were constructed by known methods. See Ausubel at §§6.3–6.4.

Glandular dissection was employed to obtain mRNA encoding a dragline spider silk protein. Major ampullate glands were dissected out of living spiders through a 1.5 cm longitudinal incision along the ventral abdomen. The glands were removed carefully to avoid degradation of the luminar contents. The glands were immediately transferred to a medium containing 0.10 M sodium chloride and 0.015 M sodium citrate (SSC). Protease inhibitors, phenylmethyl sulfonyl fluoride (PMSF) at a final concentration of 6–10mg/ml (*Methods in Enzymology* 26:3–27 (1972)), and 20 units/ml of aprotonin (Piperno et al., *Proc. Natl. Acad. Sci. USA* 74:1600–1604 (1979)) were added to the dissection buffer to inhibit proteases released by the gastric system of the spider.

Messenger RNA was isolated by known procedures from the major ampullate gland which produces almost exclusively dragline silk protein. See, e.g., Ausubel at §4. The mRNA was used to construct a cDNA library and the above-mentioned probes were used to screen the library. Id. at §§5 and 6.

The synthesized cDNA was cloned into an expression vector, the lambda gt11 Sfi-Not vector (commercially available, e.g., from Promega Biotech, Promega Corporation, Madison, WI) was employed. Lambda gt11 Sfi-Not DNA is a vector designed for orientation specific cDNA cloning which allows the expression of cloned inserts as polypeptides fused with beta-galactosidase. Directional cloning was achieved by using a unique oligodeoxynucleotide primer-adapter containing the recognition site for NotI upstream from an oligo(dT) sequence to prime first strand synthesis. After second strand synthesis and ligation of either EcoRI linkers or adapters, the double stranded molecules were digested with NotI (and EcoRI for linkers). Following removal of excess linker/adaptor fragments, the spider silk cDNA was ready to ligate into the EcoRI-NotI vector arms provided. Recombinant phage are recognized by their ability to form colorless plaques when plated on lac-hosts (*E. coli* Y1089(r-) and Y1090(r-)) in the presence of X-Gal (5-bromo-4-chloro-3-indolyl-B-galactopyranoside). By this method, all of the spider silk cDNA molecules were cloned in the same orientation relative to the lacZ gene, which effectively doubled the likelihood of in-frame expression of cloned silk genes as fusion proteins.

Dragline silk clones were isolated by using nucleic acid probes constructed specifically from dragline silk protein sequences. Once identified, these clones were repurified 3× to ensure purification of only the dragline silk cDNA. Positive clones were sequenced by conventional procedures and the overlapping sequences used to determine the full length nucleic acid sequence that encodes a dragline silk protein of Nephila. See, e.g., Ausubel at §§ 6 and 7. Next, the full length cDNA was reconstructed from the cloned fragments and was determined to have a length of 12 kb. Id. at §3.16.

EXAMPLE 6

Expression of a Spider Silk Protein

The cloned silk was expressed in *E. coli* via the vector described in Example 5 above, and the resultant silk/β-Gal fusion protein was screened with a Protoblot immunoscreening system by screening phage plaques containing the recombinant protein and by western blotting of lambda lysogens after purification on a protosorb lacZ immunoaffinity adsorbent column. The purification on the LacZ immunoaffintiy column was alternatively used to elute the silk protein, cleaved from the lacZ protein by treatment with cyanogen bromide, using increased salt concentration. The cyanogen bromide and salt were then removed from the purified silk protein by dialysis.

After full characterization of the recombinant protein (MW=350,000), it was concluded that a recombinant spider silk protein had been successfully cloned, expressed, and isolated. Comparison of amino acid composition of the recombinant protein with the endogenous protein showed that while the amino acid composition was not identical to either that of the spun spider silk or that obtained from the major ampullae, the composition was similar enough to have the same mechanostructural and other physical characteristics of the endogenous proteins.

EXAMPLE 7

Cloning and Expression of a Spider Silk Protein Variant

A variant of a spider silk protein can be generated by modification of a cDNA encoding a spider silk protein as described in Example 5, above, by known site directed or cassette mutagenesis techniques according to, e.g., Ausubel at §8. Suitable fragments of the cDNA can be modified by site directed or cassette mutagenesis to provide cDNA that encodes a dragline silk protein variant having a at least one of each of the amorphous and crystalline domains depicted in FIGS. 2 and 4, respectively. When such a cDNA is expressed according to Example 6, above, a spider silk protein variant can be expressed that has a molecular weight of about 110,000, wherein the variant comprises about 10 crystalline and 10 amorphous domains, as depicted in FIGS. 4 and 2, respectively.

EXAMPLE 8

Cloning and Expression of a Spider Silk Mutein

A mutein of a spider silk protein can be generated by modification of a cDNA encoding a spider silk protein as described in Example 5, above, by known site directed or cassette mutagenesis techniques as described by, e.g., Ausubel at §8. Suitable portions of a cDNA can be modified by site directed or cassette mutagenesis to provide cDNA that encodes a dragline silk protein mutein having a at least one of each of the amorphous and crystalline domains depicted in FIGS. 2 and 4, respectively. When such a cDNA is expressed according to Example 6, above, a spider silk protein mutein can be expressed that has a molecular weight of about 85,000 wherein the mutein comprises about 10 crystalline and 5 amorphous domains, as depicted in FIGS. 4 and 2, respectively. Such a mutein would have higher tensile strength than an endogenous spider silk protein because the ratio of crystalline domains to amorphous domains would be greater than 1.

Alternatively, a cDNA is expressed according to Example 6, above, and a spider silk protein mutein can be expressed that has a molecular weight of about 80,000 wherein the mutein comprises about 5 crystalline and 10 amorphous domains, as depicted in FIGS. 4 and 2, respectively. Such a mutein would have higher elasticity than an endogenous spider silk protein because the ratio of crystalline domains to amorphous domains would be less than 1.

What is claimed is:

1. A method for solubilizing a spider silk protein or variant comprising the steps of:
   (A) providing a sample comprising at least one spider silk protein or variant;
   (B) contacting said sample with a solution consisting essentially of propionate and hydrochloric acid in a 50—50% volume per volume ratio;
   (C) solubilizing said spider silk protein or variant in said solution to obtain a solubilized spider silk protein or variant.

2. A method according to claim 1, wherein said solubilized spider silk protein or variant is susceptible to amino-acid sequencing.

3. A method according to claim 1, wherein said hydrochloric acid is provided into said solution at a concentration of at least 6 N. concentration.

* * * * *